United States Patent [19]

McFarlane

[11] Patent Number: 5,330,434
[45] Date of Patent: Jul. 19, 1994

[54] CATHETER INTRODUCER AND METHOD OF USING SAME

[75] Inventor: Richard H. McFarlane, Geneva, Ill.

[73] Assignee: Taut, Inc., Geneva, Ill.

[21] Appl. No.: 6,927

[22] Filed: Jan. 22, 1993

[51] Int. Cl.[5] .............................................. A61M 5/178
[52] U.S. Cl. ........................................ 604/164; 604/53
[58] Field of Search ................ 604/165, 164, 20, 19, 604/21, 53, 49; 128/784, 642

[56] References Cited

U.S. PATENT DOCUMENTS

| | | | |
|---|---|---|---|
| 3,147,750 | 9/1964 | Fry | 128/642 |
| 3,540,434 | 11/1970 | Frey | 128/642 |
| 4,166,469 | 9/1979 | Littleford | 604/164 |
| 4,795,434 | 1/1989 | Kujawski | 604/164 |
| 4,805,652 | 2/1989 | Wyler | 128/642 |
| 4,824,433 | 4/1989 | Marz et al. | 604/164 |
| 5,007,902 | 4/1991 | Witt | 604/164 |
| 5,170,788 | 12/1992 | Blumenfeld | 128/642 |

Primary Examiner—John G. Weiss
Attorney, Agent, or Firm—Malloy & Malloy

[57] ABSTRACT

A catheter introducer adapted to facilitate insertion of a catheter into a patient without requiring a large aperture be made in the patient wherethrough a separate catheter may be inserted; the catheter introducer includes an elongate narrow wire adapted to pass through the catheter and be sufficiently long so as to protrude from an open distal end of the catheter, the wire being adapted to receive an electrical current charge therethrough so as to energize a protruding tip region of the wire and facilitate direct insertion of the catheter into the patient. The catheter introducer includes a removable lock head structured to be removably secured over a proximal hub portion of the catheter subsequent to insertion of the wire into the catheter, and is utilized as part of a method of inserting a catheter wherein a patient is first placed upon a grounded operating surface, the elongate wire of the catheter introducer is inserted into the catheter, current is introduced into the wire, the catheter is pushed easily through the patient's flesh as a result of contact by the energized protruding tip region of the wire with the patient's flesh, the catheter being inserted a desired distance into the patient after which the current is removed from the wire and the catheter introducer is removed from the catheter to allow normal use of the catheter.

8 Claims, 1 Drawing Sheet

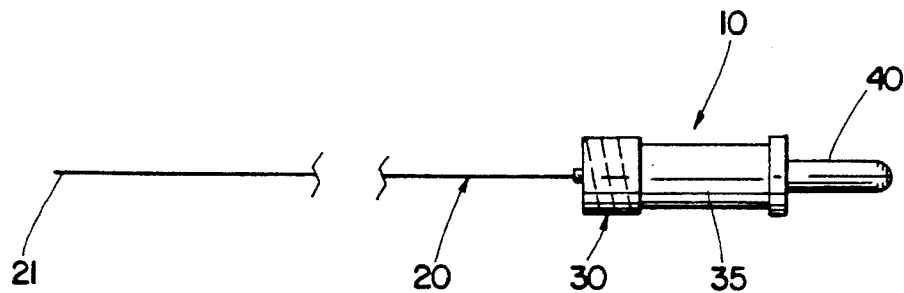
Fig. 1
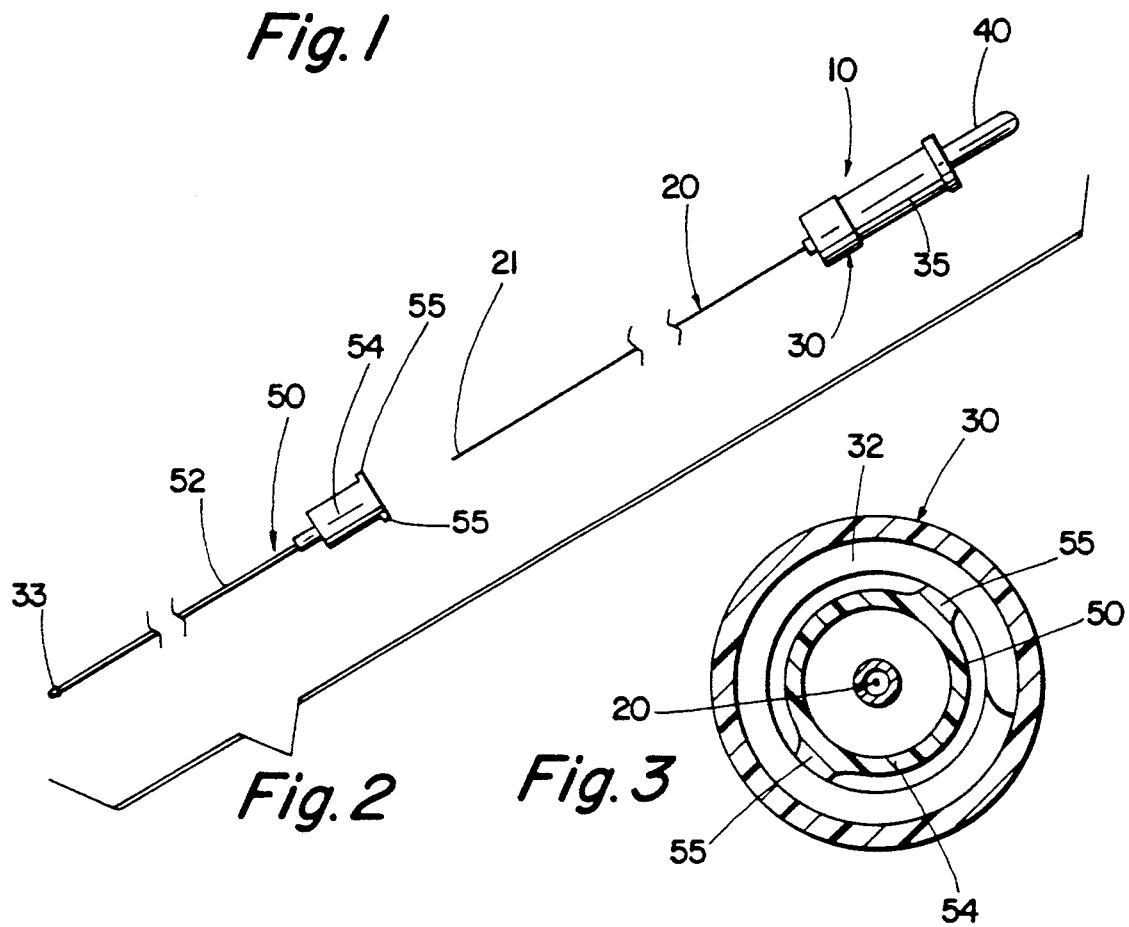
Fig. 2
Fig. 3
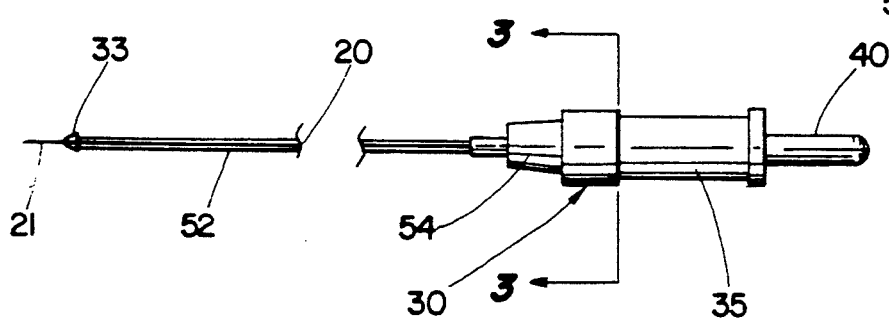
Fig. 4

CATHETER INTRODUCER AND METHOD OF USING SAME

BACKGROUND OF THE INVENTION

1. Field of the Invention

The present invention relates to a catheter introducer and method of using same adapted to enable an electrical charge to pass through a standard catheter, utilizing an elongate wire, such that the electrically energized wire facilitates insertion of the catheter directly into the patient, thereby enabling a doctor to easily and safely insert a catheter into the patient without requiring a large aperture through which the catheter would be inserted be made.

2. Description of the Related Art

More and more commonly today surgical procedures do not require large incisions in a patient wherein all must be exposed for a doctor to properly operate. Laproscopic type surgical procedures are becoming the prevalent norm because of their many benefits to the recovery of the patient. In procedures such as gallbladder surgery, a number of relatively large apertures, wherein trocars are generally inserted and maintained, are made in the patient as the primary access to the patient's interior. Through these openings, a patient's abdominal region is inflated so as to provide a more ample and convenient work area within the patient. By means of the trocars, surgical tools are inserted into the patient such that the procedures may be performed. In many procedures, such as the gallbladder procedure, catheters are utilized for particular segments of the operation. Traditionally, catheter introducers much like a smaller version of a trocar have been utilized to make an aperture within a patient wherethrough the catheter is then inserted. These extraneous openings, however, are still too large and it would be very beneficial to minimize the size of these extraneous openings whenever possible. Due to the flexible and substantially thin nature of a catheter, they have not been readily adaptable for direct insertion into the patient because that would be analogous to pushing a string into a hole in the wall. Therefore, an introducer has been utilized for catheter insertion therethrough, requiring the formation of the extraneous holes.

The device of the present invention is adapted specifically to enable the catheter itself to be inserted directly into the patient without the need for any additional, relatively large openings, thereby minimizing the size of any opening within the patient and eliminating the need for extra trocar type introducers to be utilized for each catheter that must be inserted into the patient. The catheter introducer of the present invention is adapted for use with any catheter. It is like an electric sword. It utilizes an electrically energized elongate wire that passes through the catheter tube and protrudes slightly from a tip thereof. By energizing the wire, the tip portion of the wire upon contacting the patient's flesh allows the catheter to easily pass through the patient's flesh and limits the size of the aperture directly to the diameter of the catheter. Known introducers require an opening through which the catheter is inserted and require an introducer for each catheter which is within the patient at a given time. Accordingly, a catheter introducer as that of the present invention which enables the catheter to be inserted directly and may be removed from an inserted catheter and utilized with other catheters to be inserted, provides a beneficial improvement in non-invasive type surgery.

SUMMARY OF THE INVENTION

The present invention relates to a catheter introducer and method of using the same. The catheter introducer is adapted to be utilized with a standard catheter and includes primarily an elongate, narrow wire adapted to pass through the catheter. The wire is adapted to be long enough to protrude from an open distal tip of the catheter, thereby leaving a protruding distal tip region of the wire exposed. The catheter introducer is secured to the catheter by a removable lock head structured to be disposed over a proximal hub portion of the catheter and be removably secured thereto during use of the catheter introducer. A current charge passes into the wire by electrical connection means which are connected to the wire. The electrical connection means receive the current charge from an external power source and transfer it to the wire which becomes energized to facilitate insertion of the catheter into the patient.

The catheter introducer is utilized as part of the method of inserting a catheter. The method includes the steps of placing a patient on a grounded operating surface to ensure the patient's safety, followed by inserting the elongate wire into the catheter such that the wire protrudes from a distal tip of the catheter. Next, current is introduced into the wire and the catheter is easily pushed through the patient's flesh as a result of contact by an energized protruding tip region of the wire with the patient's flesh. The catheter is inserted a desired distance into the patient, then the current is removed from the wire. Finally, the wire is removed from the catheter and the catheter may be used as normal.

It is an object of the present invention to provide a safe and effective catheter introducer which will not require an aperture larger than the diameter of the catheter itself to be made in a patient in order to introduce the catheter into the patient.

A further object of the present invention is to provide a method of inserting a catheter which does not require a specialized catheter to be utilized in order to insert the catheter directly into the patient and without the need of the previous formation of an insertion aperture or trocar.

Still another object of the present invention is to provide a catheter introducer which may be utilized with a standard catheter and enables the catheter to be used as normal.

BRIEF DESCRIPTION OF THE DRAWINGS

For a fuller understanding of the nature of the present invention, reference should be had to the following detailed description taken in connection with the accompanying drawings in which:

FIG. 1 is a side view of the catheter introducer of the present invention.

FIG. 2 is an exploded view of the catheter introducer of the present invention and the catheter into which it will be inserted.

FIG. 3 is a cross-sectional view along line 3—3 of FIG. 4.

FIG. 4 is a side view of the catheter introducer positioned within a catheter for use.

Like reference numerals refer to like parts throughout the several views of the drawings.

DETAILED DESCRIPTION OF THE PREFERRED EMBODIMENT

Shown throughout FIGS. 1-4, the present invention is directed towards a catheter introducer, generally indicated as 10. The catheter introducer 10 is adapted to be utilized with a standard catheter 50 so as to enable the catheter 50 to be directly inserted into a patient without the need for forming a large aperture or use of a trocar or introducer through which a catheter is inserted. The catheter introducer 10 includes primarily an elongate electrically conductive wire 20. The wire 20 is substantially narrow, in the preferred embodiment, having a cross-sectional diameter of about 0.015". The wire 20, see FIG. 3, is adapted to pass through the catheter 50, and extend through and beyond the catheter lumen or tube 52 so as to protrude from an open distal tip 53 of the catheter tube 52. The catheter introducer 10 further includes a removable head 30 structured to be disposed over the proximal hub portion 54 of the catheter 50. As best illustrated in FIG. 3, the removable head 30 may include a threaded interior 32 which is adapted to receive the flanged portions 55 extending from the hub portion 54 of the catheter 50 therein, thereby removably, yet securely attaching the catheter 50 to the catheter introducer 10. Any other type connecting means may be utilized. Extending through the removable head 30 is an axial opening 34 wherethrough the wire 20 passes and connects with electrical connection means that receive a current charge from an external power source and transfer it to the wire 20. The electrical connection means primarily include a protruding terminal stud 40 which is connected to the external power source, such as an electro surgical generator as is commonly employed in laproscopic surgical procedures. The terminal stud 40 receives the current charge and transfers it through the wire 20 such that a protruding tip 21 of the wire 20 becomes energized and may be utilized to contact the patient's flesh and facilitate insertion of the catheter 50 directly into the patient. In order to facilitate manipulation of the catheter introducer 10 while the current charge is flowing, insulated grasping and manipulating means 35 are disposed between the head 30 and the terminal stud 40. The grasping and manipulating means 35 which are preferably in the form of an extended hub, as shown in the preferred embodiment, enables a user to hold the catheter introducer 10 without being shocked. Of course, the catheter wall provides an insulation means and hence the device may be grasped anywhere along the catheter length.

This catheter introducer 10 is utilized as a method of inserting a catheter 50, which does not require the prior insertion of a tubular type inserter which forms a large opening within the patient. Generally, when abdominal operations, such as gallbladder surgery are performed, a catheter 50 must be independently inserted into a patient so as to properly be oriented and manipulated. In the method of the present invention, the patient is placed on a grounded operating surface where he is prepped for normal surgery. Next, if necessary, as a preliminary step in the procedure, including the patient's abdominal region is inflated so as to provide a freer work space within the patient. Once the patient is prepared for surgery and has been placed on the grounded operating surface, an elongate wire 20, of the catheter introducer 10 of the present invention, is inserted into the catheter 50 such that the wire 20 protrudes from the distal tip 53, which tip may be provided with a somewhat enlarged or afrowed tip. Next, current is introduced to the wire 20, such as by means of an electro surgical generator, which are common, such as the Valley Labs, Inc. Unit No. 4. The catheter is then easily introduced by pushing the wire tip through the patient's flesh as a result of contact by the energized protruding tip region 21 of the wire 20 contacting the patient's flesh and essentially making a small sized hole. The diameter of the wire is preferably about 0.016", and about 50 watts energy is utilized. The correct setting of the energy supplied by any such machine may be selected by several insertions of the introducer in the large piece of meat. Through this small hole in the patient, the head 53 of the catheter 50 follows dilating the hole to accommodate the diameter of the catheter, usually about 0.060" as it follows the wire tip, passing with great ease. The catheter 50 is inserted a desired distance into the patient and then the current is removed from the wire 20. Finally, the wire 20 is removed from the catheter 50 and the catheter 50 may be utilized as normal for the desired surgical procedure.

It is thus seen that the electrically charged wire constitutes the introducer and it is within the catheter, instead of the prior tubular introducers, which are, in effect, needles which jacket the catheter; that is to say in this invention the introducer is in the catheter and not outside of the catheter.

In one preferred embodiment, the catheter and wire introducer are pre-assembled as a combination. In cholangiography procedures, the catheter is about one to one and one-half feet in length.

Now that the invention has been described,
What is claimed is:

1. In combination with a flexible catheter of a predetermined length having a) a distal end, b) a proximal end with a hub, and c) a lumen extending between the ends, a catheter introducer comprising:

an elongate, narrow, flexible, electrically conductive wire having a distal end zone and a proximal end zone and being sized for passage through the catheter and said wire being of a length slightly greater than the predetermined length of the catheter axially through the lumen, so that the distal end zone of the wire protrudes from the lumen at the distal end of the catheter defining a distal wire tip, a hub on the proximal end zone of the wire comprising means to cooperate with the catheter to resist movement of the wire tip into the catheter upon insertion into a patient, and electrical connection means connected to said wire, said electrical connection means being connected to said wire, said electrical connection means being structured and disposed to receive a current charge from an external power source and transfer it to said distal wire tip such that said distal wire tip, upon being energized, enables the catheter to pass directly into the patient.

2. A catheter introducer as set forth in claim 1 wherein said hub includes a threaded interior surface structured and disposed to be secured about the proximal end hub of the catheter.

3. A catheter introducer as set forth in claim 2 wherein said hub includes an axial opening wherethrough said wire passes to connect with said electrical connection means.

4. A catheter introducer as set forth in claim 3 wherein said electrical connection means includes a protruding terminal zone structured and disposed to be connected with the external power source.

5. A catheter introducer as set forth in claim 1 including insulated grasping and manipulating means disposed between said hub and said electrical connection means, said insulated grasping and manipulating means being structured and disposed to be safely held to manipulate the catheter while said current charge is passing through said electrical connection means and said wire.

6. A method of inserting a catheter having a distal tip into a patient comprising the steps of:
   placing the patient on a grounded operating surface,
   orienting an elongate wire into the catheter such that a wire tip protrudes from the distal tip of the catheter,
   introducing current into said wire,
   pushing the catheter easily through the patient's flesh as a result of contact by an energized protruding wire tip of said wire with the patient's flesh,
   inserting the catheter a desired distance into the patient,
   removing the current from said wire, and
   removing said wire from the catheter to allow normal use of the catheter.

7. In combination, a cholangiogram catheter of a predetermined length of between about one to one and one-half feet in length having a) a distal end, b) a proximal end with a hub, and c) a lumen extending between the ends, and
   a catheter introducer comprising:
      an elongate, narrow, electrically conductive axially moveable wire in the lumen and having a distal end zone and a proximal end zone, said wire being of a length slightly greater than the predetermined length of the catheter axially through the lumen, so that the distal end zone of the wire protrudes from the lumen at the distal end of the catheter defining a distal wire tip of about one quarter of an inch in length,
      a hub on the proximal end zone of the wire comprising means to cooperate with the catheter to resist movement of the wire tip into the catheter upon insertion into a patient, and
      electrical connection means connected to said wire, said electrical connection means being structured and disposed to receive a current charge from an external power source and transfer it to said wire tip zone.

8. The combination as set forth in claim 7 wherein the distal end of the catheter is arrow-shaped defining a shoulder adjacent the distal end.

* * * * *